United States Patent
Thunnissen et al.

(10) Patent No.: US 7,531,305 B2
(45) Date of Patent: May 12, 2009

(54) HUMAN PAPILLOMA VIRUS DETECTION WITH DNA MICROARRAY

(75) Inventors: Eric Fredericus Bernardus Josephus Mar Thunnissen, Beuningen (NL); Cornelis Hendrikus Wilhelm Klaassen, Wijchen (NL); Clemens Franciscus Maria Prinsen, Nijmegen (NL)

(73) Assignee: Autogenomics, Inc., Cansbad, CA (US)

( * ) Notice: Subject to any disclaimer, the term of this patent is extended or adjusted under 35 U.S.C. 154(b) by 319 days.

(21) Appl. No.: 10/511,284

(22) PCT Filed: Apr. 16, 2003

(86) PCT No.: PCT/EP03/03984

§ 371 (c)(1), (2), (4) Date: Apr. 21, 2005

(87) PCT Pub. No.: WO03/087829

PCT Pub. Date: Oct. 23, 2003

(65) Prior Publication Data

US 2008/0153081 A1 Jun. 26, 2008

(51) Int. Cl.
*C12Q 1/68* (2006.01)
*C07H 21/04* (2006.01)
*C12P 19/34* (2006.01)

(52) U.S. Cl. .................. 435/6; 536/23.1; 536/24.32; 536/24.33; 435/91.2

(58) Field of Classification Search ........................ None
See application file for complete search history.

(56) References Cited

U.S. PATENT DOCUMENTS 5,182,377 A * 1/1993 Manos et al. .................. 435/6
5,925,525 A * 7/1999 Fodor et al. ..................... 435/6

OTHER PUBLICATIONS

GenBank GI:397060 [online] Aug. 22, 1993 [retrieved on Sep. 23, 2008] http://www.ncbi.nlm.nih.gov/entrez/viewer.fcgi?397060:OLDID:456557.*
GenBank GI:60955 [online] Jul. 6, 1989 [retrieved on Sep. 23, 2008] http://www.ncbi.nlm.nih.gov/entrez/viewer.fcgi?60955:OLDID:34726.*
GenBank GI:940299 [online] Aug. 8, 1995 [retrieved on Sep. 23, 2008] http://www.ncbi.nlm.nih.gov/entrez/viewer.fcgi?db=nuccore&id=940299.*
GenBank GI:6002612 [online] Oct. 1, 1999 [retrieved on Sep. 23, 2008] http://www.ncbi.nlm.nih.gov/entrez/viewer.fcgi?6002612:OLD08:69388.*
GenBank GI:4103240 [online] Jan 5, 1999 [retrieved on Sep. 23, 2008] http://www.ncbi.nlm.nih.gov/entrez/viewer.fcgi?db=nuccore&id=4103240.*
GenBank GI:333026 [online] Jun. 2, 1994 [retrieved on Sep. 23, 2008] http://www.ncbi.nlm.nih.gov/entrez/viewer.fcgi?db=nuccore&id=333026.*
GenBank GI:1020266 [online] Oct. 17, 1995 [retrieved on Sep. 23, 2008] http://www.ncbi.nlm.nih.gov/entrez/viewer.fcgi?db=nuccore&id=1020266.*
GenBank GI:1020242 [online] Oct. 17, 1995 [retrieved on Sep. 23, 2008] http://www.ncbi.nlm.nih.gov/entrez/viewer.fcgi?db=nuccore&id=1020242.*
GenBank GI:60295 [online] Jan. 7, 1993 [retrieved on Sep. 23, 2008] http://www.ncbi.nlm.nih.gov/entrez/viewer.fcgi?60295:OLDID:34483.*
GenBank GI:396981 [online] Aug. 22, 1993 [retrieved on Sep. 23, 2008] http://www.ncbi.nlm.nih.gov/entrez/viewer.fcgi?396981:OLDID:456547.*
GenBank GI:333211 [online] Feb. 23, 1994 [retrieved on Sep. 23, 2008] http://www.ncbi.nlm.nih.gov/entrez/viewer.fcgi?396981:OLDID:456547.*
Edwards et al. Pentanucleotide repeat length polymorphism at the human CD4 locus. Nucleic Acids Research 19(17):4791 (1991).*
Butler JM. Short tandem repeat analysis for human identity testing. Current Protocols in Human Genetics (2004) 14.8.1-14.8.22, John Wiley & Sons, Inc.*

* cited by examiner

*Primary Examiner*—Gary Benzion
*Assistant Examiner*—Samuel Woolwine
(74) *Attorney, Agent, or Firm*—Fish & Associates, PC

(57) ABSTRACT

A method is provided of detecting the presence of HPV comprising the following steps: a. amplification and labelling part of the E1 HPV gene, in particular its 3' end; b. hydrizing the labelled fragment to a solid support containing microarrays with various HPV specific capture probes; c. removing uncaptured labeled fragments; d. detecting captured detectable moiety indicating the presence of HPV sequence DNA in a sample. Further provided is a test kit for carrying out said detection method.

10 Claims, 3 Drawing Sheets

Example of a HPV16 detection

Fluorescence

Sensitivity >

HPV 16 >
Detection Ctl >

Absorption

Sensitivity >

HPV 16 >
Detection Ctl >

SEQUENCE LISTING

<160> NUMBER OF SEQ ID NOS: 59

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(20)

<400> SEQUENCE: 1
gtgccaggaw cagttgttag                                              20

```
<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(18)

<400> SEQUENCE: 2
cawktghatt tcaatdgc                                                    18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(20)

<400> SEQUENCE: 3
cagttgttag aactktatga                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(20)

<400> SEQUENCE: 4
tcytgyaahg tccahggytc                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(20)

<400> SEQUENCE: 5
gaaatsvtty ttymraaggt                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(20)

<400> SEQUENCE: 6
tcctggcacr catctaaacg                                                  20
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: based on
     genomic DNA sequence from Human Papilloma Virus
<220> FEATURE:
<221> NAME/KEY: primer_bind
<222> LOCATION: (1)..(23)

<400> SEQUENCE: 7
tttbhaaatv catttccawt wga                                          23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: based on
     genomic DNA sequence from Human Papilloma Virus
<220> FEATURE:
<221> NAME/KEY: primer_bind
<222> LOCATION: (1)..(24)

<400> SEQUENCE: 8
taaacghtkr sahagnktct ccat                                         24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: based on
     genomic DNA sequence from Human Papilloma Virus
<220> FEATURE:
<221> NAME/KEY: primer_bind
<222> LOCATION: (1)..(20)

<400> SEQUENCE: 9
cctttttctc aaggacgtgg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: based on
     genomic DNA sequence from Human Papilloma Virus
<220> FEATURE:
<221> NAME/KEY: primer_bind
<222> LOCATION: (1)..(20)

<400> SEQUENCE: 10
cdtggtscar attagayttg                                              20

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: based on
     genomic DNA sequence from Human Papilloma Virus
<220> FEATURE:
<221> NAME/KEY: primer_bind
<222> LOCATION: (1)..(18)

<400> SEQUENCE: 11

-continued gnhgghacca cbtggtgg                                              18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(20)
<220> FEATURE:
<221> NAME/KEY: modified_base
<222> LOCATION: (2)
<223> OTHER INFORMATION: i
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (10)
<223> OTHER INFORMATION: i
<220> FEATURE:
<221> NAME/KEY: modified_base
<222> LOCATION: (17)
<223> OTHER INFORMATION: i

<400> SEQUENCE: 12
cntggtncan attaganttg                                            20

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(18)
<220> FEATURE:
<221> NAME/KEY: modified_base
<222> LOCATION: (2)..(3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i

<400> SEQUENCE: 13
gnnggnacca cntggtgg                                              18

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(22)
<220> FEATURE:
<221> NAME/KEY: modified_base
<222> LOCATION: (5)
<223> OTHER INFORMATION: i
<220> FEATURE:
<221> NAME/KEY: modified_base

```
<222> LOCATION: (8)..(9)
<223> OTHER INFORMATION: i
<220> FEATURE:
<221> NAME/KEY: modified_base
<222> LOCATION: (11)
<223> OTHER INFORMATION: i
<220> FEATURE:
<221> NAME/KEY: modified_base
<222> LOCATION: (20)
<223> OTHER INFORMATION: i

<400> SEQUENCE: 14
twgsnytnnt ngatgaygyn ac                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(22)
<220> FEATURE:
<221> NAME/KEY: modified_base
<222> LOCATION: (2)
<223> OTHER INFORMATION: i
<220> FEATURE:
<221> NAME/KEY: modified_base
<222> LOCATION: (5)
<223> OTHER INFORMATION: i
<220> FEATURE:
<221> NAME/KEY: modified_base
<222> LOCATION: (8)
<223> OTHER INFORMATION: i
<220> FEATURE:
<221> NAME/KEY: modified_base
<222> LOCATION: (20)
<223> OTHER INFORMATION: i

<400> SEQUENCE: 15
tngsnytnwt rgatgatgcn ac                                              22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(22)
<220> FEATURE:
<221> NAME/KEY: modified_base
<222> LOCATION: (2)
<223> OTHER INFORMATION: i
<220> FEATURE:
<221> NAME/KEY: modified_base
<222> LOCATION: (5)
<223> OTHER INFORMATION: i
<220> FEATURE:
<221> NAME/KEY: modified_base
<222> LOCATION: (8)..(9)
<223> OTHER INFORMATION: i
<220> FEATURE:
<221> NAME/KEY: modified_base
<222> LOCATION: (11)
<223> OTHER INFORMATION: i
<220> FEATURE:
<221> NAME/KEY: modified_base
<222> LOCATION: (20)
<223> OTHER INFORMATION: i
```

```
<400> SEQUENCE: 16
tngsnytnnt ngatgaygyn ac                                      22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(20)

<400> SEQUENCE: 17
gatttccagc tttggtcagt                                         20

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(27)
<220> FEATURE:
<221> NAME/KEY: modified_base
<222> LOCATION: (22)
<223> OTHER INFORMATION: i

<400> SEQUENCE: 18
ccamarcctt tyaaaraaag ankycca                                 27

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(26)
<220> FEATURE:
<221> NAME/KEY: modified_base
<222> LOCATION: (10)
<223> OTHER INFORMATION: i
<220> FEATURE:
<221> NAME/KEY: modified_base
<222> LOCATION: (21)
<223> OTHER INFORMATION: i

<400> SEQUENCE: 19
smaaryttkn kraaaaaasa nktcca                                  26

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(22)

<400> SEQUENCE: 20
tngsnytnht dgatgaygyn ac                                      22
```

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(27)

<400> SEQUENCE: 21
ssmmaryytk hbraaraaas abkycca                                          27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(27)

<400> SEQUENCE: 22
ccamarcctt tyaaaraaag abkycca                                          27

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: based on
      genomic DNA sequence from Human Papilloma Virus
<220> FEATURE:
<221> NAME/KEY: primer_bind
<222> LOCATION: (1)..(26)

<400> SEQUENCE: 23
vmaaryttkh kraaaaaasa bktcca                                           26

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 24
ttttcttttc ttttcagagg agcaggacga caatg                                 35

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 25
ttttcttttc ttttctgaag acgaggagga caatg                                 35

<210> SEQ ID NO 26

```
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 26
ttttcttttc ttttcccatt aaaggtgtcc gaagc                            35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 27
ttttcttttc ttttcagatg tgtcaaaagc caaag                            35

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 28
ttttcttttc ttttccgagg aggagcatgg aaacc                            35

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 29
ttttcttttc ttttcccatt aactgtgtca gagac                            35

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 30
ttttcttttc ttttcattga cagtatcaca agcta                            35

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 31
```
ttttcttttc ttttccagac ctacgtgacc atata          35

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 32
ttttcttttc ttttcacatg gcatacagac attaa          35

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 33
ttttcttttc ttttcgagga aaatggaaac cctag          35

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 34
ttttcttttc ttttctagta aacgactttg tgatc          35

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 35
ttttcttttc ttttcagcac tggaaatatc caggg          35

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 36
ttttcttttc ttttcctttta ttgtatacag ccaaa          35

<210> SEQ ID NO 37
<211> LENGTH: 35
<212> TYPE: DNA
<213> ORGANISM: Artificial Sequence
<220> FEATURE:

```
<223> OTHER INFORMATION: Description of Artificial Sequence: detection
      probe, based on genomic DNA sequence from Human
      Papilloma Virus

<400> SEQUENCE: 37
ttttcttttc ttttcagtaa tggaaatcca ctata                              35

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 38
ttttcttttc ttttctagca catgtttgtc tgatc                              35

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: detcetion
      probe, based on genomic DNA sequence from Human
      Papilloma Virus

<400> SEQUENCE: 39
ttttcttttc ttttcagaat actatgaaca agaca                              35

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 40
ttttcttttc ttttcagatg tttcaaaggc taaag                              35

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 41
ttttcttttc ttttcaacat tggaaacatg tagag                              35

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 42
ttttcttttc ttttcgaaat gtatacgata tgaat                              35
```

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 43
ttttcttttc ttttcacatg gtattaccaa actaa                                 35

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 44
ttttcttttc ttttcttttg ttttacaaag caaag                                 35

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 45
ttttcttttc ttttctttag cgctgaacga caacg                                 35

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 46
ttttcttttc ttttctgtta ttacacaaag caaag                                 35

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 47
ttttcttttc ttttcgtttc tttacaagga cgtgg                                 35

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

```
<400> SEQUENCE: 48
ttttcttttc ttttcagagg atcaggaaga caatg                              35

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 49
ttttcttttc ttttcctata atgtatacag ccaga                              35

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 50
ttttcttttc ttttcagaca ttaatgaaca cataa                              35

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 51
ttttcttttc ttttcagagg gatctgatca acagg                              35

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 52
ttttcttttc ttttcctttg tattataaag ctaaa                              35

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 53
ttttcttttc ttttcagttt tttttccacc acttg                              35

<210> SEQ ID NO 54
<211> LENGTH: 35
<212> TYPE: DNA
<213> ORGANISM: Artificial Sequence
```

-continued

```
<220> FEATURE:
<223> OTHER INFORMATION: Description of Artificial Sequence: detection
      probe, based on genomic DNA sequence from Human
      Papilloma Virus

<400> SEQUENCE: 54
ttttcttttc ttttcagaac attatgaaca ggaca                              35

<210> SEQ ID NO 55
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 55
ttttcttttc ttttcagagg gacctgacga acagg                              35

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 56
ttttcttttc ttttcagtaa tgggaaccca ctata                              35

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 57
ttttcttttc ttttctatat gcactaaatg atgta                              35

<210> SEQ ID NO 58
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 58
ttttcttttc ttttctttag aattgcatca agagg                              35

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: detection
      probe, based on genomic DNA sequence from Human
      Papilloma Virus

<400> SEQUENCE: 59
ttttcttttc ttttcaacat tacgagactg atagt                              35
```

HUMAN PAPILLOMA VIRUS DETECTION WITH DNA MICROARRAY

FIELD OF THE INVENTION

The present invention is in the field of molecular biology and diagnostics, and relates in particular to an improved diagnostic procedure for the detection of Human Papilloma Virus (HPV) types using DNA microarray techniques. The diagnostic method is useful for the detection of any known HPV types, for example, in the early detection of (pre)neoplastic epithelial lesions in uterine cervix, and tumors of skin, head and neck and other sites.

BACKGROUND OF THE INVENTION

Cancer is the second overall leading cause of death, after ischemic heart disease, in the United States and Western Europe and despite recent advances in its treatment, there is, for most cancer types, no miracle cure on the horizon. Cancer causes approximately 25% of all deaths. The incidence continues to rise, probably reflecting the increasing average age of the population. The key to survival is early diagnosis and treatment.

About two decades ago HPV was associated with human tumors. Since then it has been detected in tumors and (pre) neoplastic lesions of different sites such as uterine cervix, penis, skin, middle ear, anus, squamous cell tumours of the head and neck region (oral mucosa, tonsil, larynx, pharynx), lung, urinary bladder.

More than 70 different types of HPV have been reported with different relations to the progression of a lesion. Some of the types have stronger association with the progression to malignant tumors than others e.g. type 16 and 18 are associated with high grade intraepithelial dysplasia of the cervix. These are called 'high risk' HPV types. The number of HR-HPV has been expanded the last years to e.g. 16, 18 45, 31, 33 . Other types are mainly associated with benign tumors such type such as 1,2, 4, 5, and 6 with benign skin warts. HPV type 11 is frequently present in juvenile recurrent respiratory papillomas. Frequently in a series of cases of one histologic type of lesion different HPV types have been detected. Occasionally, multiple HPV types were found within one lesion (coinfection). In erythroplasia of Querat HPV type 8 was found in combination with other types of HPV [Wieland 2000]. In renal transplant recipients the number of keratotic lesions increases after several years. Also in these lesions a wide range of HPV types are recognized [De Jong-Tieben 2000]. In Epidermodysplasia Verruciformis HPV type 47 has been shown [Adachi 1996]. In Global nail dystrophy type 57 infection was found. [McCown 1999]

Although several different types have been described, recently minor variations in DNA composition have been within one type. Because of the genetic diversity of HPV the use of type-specific amplification is impractical for epidemiologic studies, for which accurate typing is essential.

Within the HPV region many gene sequences have been described both at the DNA and protein level such as E1, E2, E3, E4, E5, E6, E7, L1 and L2. Several methods use the one or more of the genes above such as PGMY LBA, $SPF_{10}$ LiPA GP5+16+ combination Only one is using another E1 region than our invention does.

Several methods exist for the detection of HPV in general as well as for typing. Many use the polymerase chain reaction (PCR) for amplification of part of the HPV genome. For the PCR type specific primers can be used. As an alternative primers are used that allow amplification of more than one types. In some HPV tests primers are intended to amplify all types (general primers). These primers can be degenerated to a limited extent. With this approach one or more combinations of primers intend to cover for all HPV types (Jacobs, et al. J Clin Microbiol 1997 35:791-795; Bauer, et al., JAMA 1991 265:472477). After PCR sequencing can be performed for HPV typing. An alternative approach is to hybridise the DNA fragments to a filter containing different areas with different DNA fragments. Each area contains then DNA corresponding to one type. However, cross hybridisations may occur. In theory all different HPV types may be amplified and sequenced individually, but depending on the amount of types and variations to be known this will be an increasing amount of work.

Other approaches for the detection of HPV types are the use of restriction fragment length polymorphism analysis combined with an amplification technique, and another alternative for the detection of HPV is the use of an amplification technique in combination with single stranded conformational polymorphism (Mayrand, J Clin Microbiol 2000 38:3388-3393). Still other approaches are hybrid capture II and Ligase chain reaction (Yamazaki, et al., Int J Cancer 2001 94:222-227).

Yet approaches is to detect HPV is by in situ hybridisation (AmorTegui, et al., 1990 23:301-306; Unger, et al., J Histo chem. Cytochem 1998 46:535-540; Lizard, et al., J Virol. Methods 1998 72:15-25)) or in situ PCR (Jean-Shiunn Shyu J Surg Oncol 2001 78:101-109). On one histologic slide or cytologic specimen HPV type specific DNA fragments are necessary to obtain a signal. Thus, in theory recognition of any HPV types at least a similar number of slides/specimens is required to examine one kind of biologic sample. This would be a very laborious procedure.

Recent developments show after a PCR the use of a line probe or line blot assay to detect different types. Comparison of different line probes assays (PGMY LBA and $SPF_{10}$ LiPA) reveals a difference in sensitivity for one assay: with PGMY LBA more HPV types 42, 56 and 59 and with $SPF_{10}$ LiPA more HPV types 31 and 52 were detected [Van Doom 2002]. Also for the GP5+/6+ primers a reverse line blot assay has recently been described detecting 37 mucosal types [Van den Brule 2002 J Clin Microbiol 2002 40:779-787]. The concordance between different methods is moderate (Meyer et al. Dermatiology 2000 201:204-211; Vernon J Clin Mircobiol 2000 38:651-655).

Recently, 'chip' technology has been developed (see, e.g., U.S. Pat. No. 5,445,934). The term 'microarray' or 'chip' technology as used herein, is meant to indicate analysis of many small spots to facilitate large scale nucleic acid analysis enabling the simultaneous analysis of thousands of DNA sequences. This technique is seen as an improvement on existing methods, which are largely based on gelelectrophoresis. For a review, see *Nature Gen.* (1999) 21 Suppl. 1. Line blot assay and microarray methods both use circumscribed areas containing specific DNA fragments. As will be known in the art, line blotting is usually performed on membranes (Gravitt, et al., J Clin Microbiol 1998 36:3020-3027, whereas microarray is usually performed on a solid support and may also be performed on smaller scale.

The utility of DNA arrays for genetic analysis has been demonstrated in numerous applications including mutation detection, genotyping, physical mapping and gene-expression monitoring. The basic mechanism is hybridization between arrays of nucleotides and target nucleic acid.

Recently, the Point-EXACCT method was transferred to DNA microarray format, where a glass support is homogeneously streptavidin-coated. This coating is used to spot biotinylated probe to the glass slide and to hybridize a single-stranded target DNA to this nucleic acid probe. For detection a second probe is added, or the single stranded DNA is already labeled. The use of streptavidin-coated slides for microarray analysis is disclosed in WO 02/44713 the contents of which are incorporated herein by reference.

In conclusion, HPV types can be discerned with various laborious techniques. The present invention provides a further improvement of the microarray technique with coverage of any known HPV types on the array.

SUMMARY OF THE INVENTION

In one aspect of the invention, a combination of oligonucleotides is used, allowing amplification of a part of the E1 HPV gene. This part of the sequence has thus far not been used for HPV typing before. Especially preferred is the 3' end of the E1 HPV gene, in particular a region between about 29 to about 188 nucleotides from the 3' terminus of the E1 gene. The size of the whole gene varies from 1820 to 1964 nucleotides.

In a further aspect of the invention the examination of integration of HPV in human DNA a combination of E1 region with another HPV region such as E6 or L1 is suitable.

In a further aspect of the invention microarray is used for detection of the specific HPV type(s) after the amplification.

In a further aspect of the invention the system allows rapid reading with absorption in regular light microscope suitable for detecting and typing HPV in one procedure.

These and other aspects of the invention will be outlined in some more detail in the following description.

DETAILED DESCRIPTION OF THE INVENTION

Figure 1:
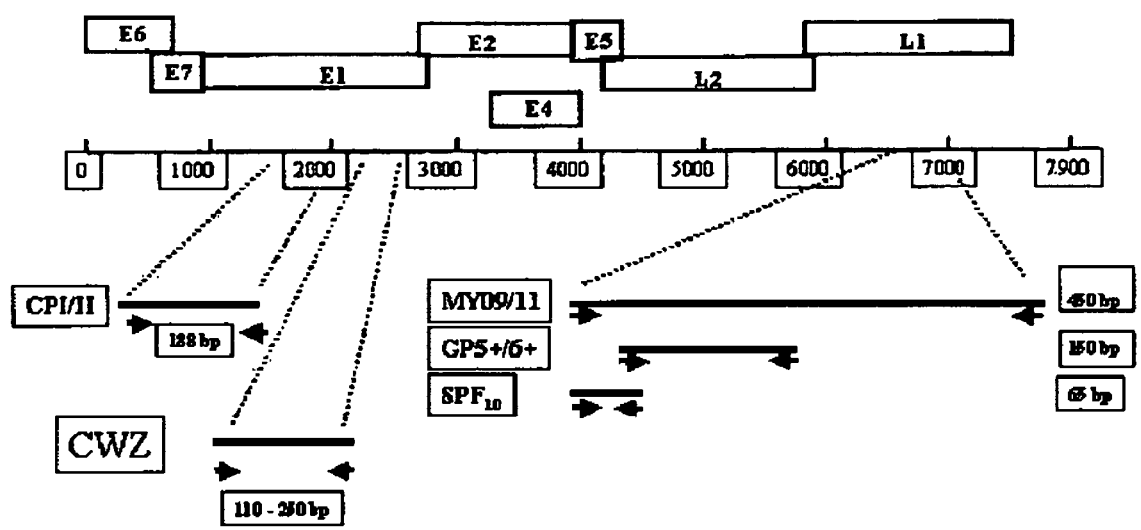
FIG. 1 depicts a schematic representation of HPV sequences containing regions with general primers sets. The schematic representation is modified from an image presented by Kleter, Utrecht, on 24 Jan. 2002. The position from the CWZ primers in the E1 region is distinctly different from other sites.
Figure 2:
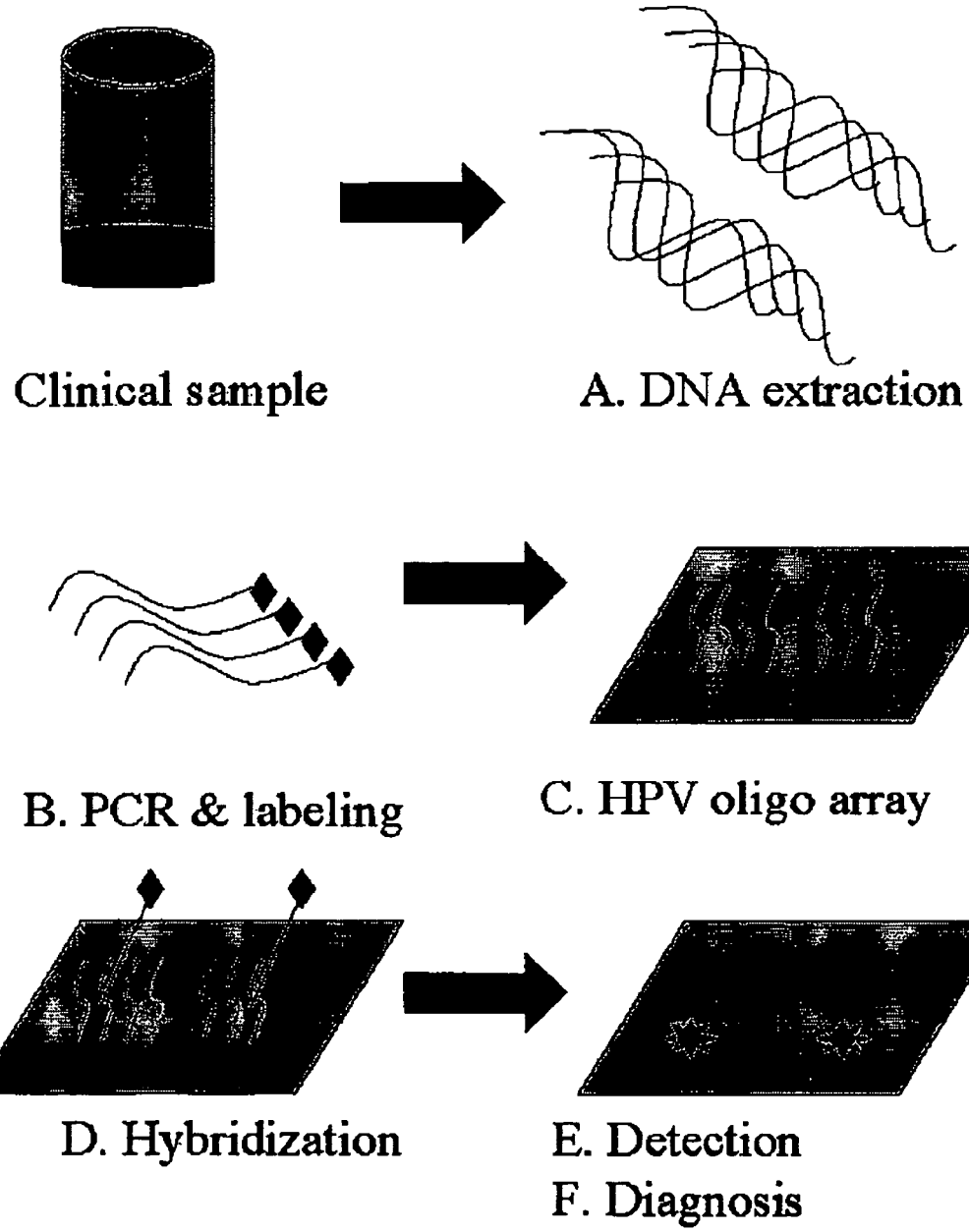
FIG. 2 depicts a schematic representation of the microarray procedure. From a clinical sample or other sample DNA is extracted (A), amplified and labeled (B). parallel a micro array has been prepared containing all HPV subtypes (C). Labeled DNA is hybridized to the array (D). DNA and other components that are not attached are washed away. Remaining fragments are hybridized based on corresponding HPV sequences and visualized based on the presence of the label. Then the spots with label may be discerned from those without label and used for HPV type detection (E,F).
Figure 3:
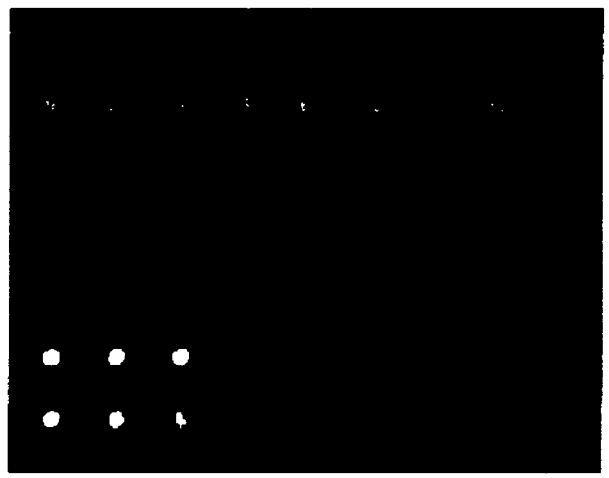
FIG. 3 shows an example of HPV 16 detection in the fluorescence and absorption mode.
Detection ctl>=positive control in triplicate.
HPV 16>=spots with capture probes for HPV 16 in triplicate visualized as described in the procedure.
Sensitivity>=signal of three different concentrations of HPV capture probes in triplicate.

The present invention provides a significant improvement of the method of detecting HPV. A new combination of oligonucleotides for HPV detection is used for amplification and detection.

The term amplification product denotes a specific fragment of double stranded DNA that arises in a process aimed at the multiplication of that fragment. All known methods for amplification are incorporated.

The term HPV specific is used herein for the combination of primer sets and detection probe. The length of the detection probe may be too short to be specific for HPV in itself, if examine against all information in gene banks. However, after amplification with HPV specific probes the chance of detecting labeled DNA other than HPV is neglectable. The oligonucleotides for capturing may, therefore, not be unique.

The term primer and probe as used herein denote oligonucleotides. Primer is used for the single stranded DNA fragment that is used for amplification. Probe is used for the single stranded DNA fragment that has a capture function on the solid support. The term "detection probe" as used herein emphasizes the capturing function.

The term degenerate primer or probe denotes an oligonucleotide with at certain positions either a mixture of different nucleotides or a base analogue.

The terms incubation of proteins and hybridisation of nucleic acids have similar components i.e. diffusion and binding of molecules to there specific targets. With diffusion, as used herein, the same process is meant for nucleic acids, proteins and other molecules interacting with a target on the solid support.

The term visualization denotes any way that in a non-radioactive fashion a hybridization product with hapten can be visualized with any microscope system.

The target on the solid support consists of solid part with attached i.e. immobilized one or more different kinds of molecules, such as nucleic acids, proteins, whole cells, sections of cells or tissues.

The terms incubation chamber and hybridisation chamber, as used herein, are synonyms and are meant to indicate the three dimensional space above the target present on the solid support, where the solid support is an integral part of the incubation/hybridisation chamber.

The terms 'microarray' or 'chip' technique or technology, as used herein, are synonyms and are meant to indicate analysis of a plurality of small spots of nucleic acids distributed on a small surface area to facilitate large scale nucleic acid analysis enabling the simultaneous analysis of thousands of DNA and/or RNA sequences. The terms are likewise applicable to the analysis of peptides or proteins in a similar way.

The term incubation fluid is meant to indicate the fluid containing e.g. the substrate to be bound on the solid support.

The term test fluid is meant to indicate the volume of any fluid component necessary for the experiment/test to be carried out with the flow through system.

The terms immunohistochemistry and immunocytochemistry, are meant as synonyms, indicating the binding of antibodies to haptens, usually parts of tissues or cells present on the solid support, but also as used herein it is the visualization procedure after binding to the hapten.

The terms low and high risk HPV denote a difference in association with the chance of development of malignancy. This has especially for the uterine cervix been described. For high risk is the chance of development of malignancy is higher than for the low risk HPV types.

All reported HPV gene sequences in October 2000 (E1, E2, E4, E5, E6, E7, L1 and L2) (both at the DNA and protein level) were separately and systematically analyzed to select a region of the HPV genome that allowed subdivision of all HPV types into clusters of HPV types. Based on sequence homology at the protein and/or DNA level, several previously unassigned HPV types putatively can be assigned either as low risk or high risk HPV. The subdivision of all HPV types intended to make an as large as possible distinction between low and high risk mucosal types of HPV.

The following criteria were used. Each cluster had to contain at least two regions with a relative high degree of DNA sequence homology between the different HPV types in that cluster to allow the formulation of 'common' PCR primers. In addition, these potential PCR primer location sites should differ as much as possible between different clusters to allow amplification of cluster-specific and/or risk-specific HPV types. Another criterium was that between the potential PCR-primer locations, sufficient heterogeneity between the DNA sequences is present to select DNA sequences that allow for discrimination between different HPV types. Based on these criteria, the HPV E1 gene was chosen for design of the assay. Subsequently, three major groups of HPV types were discriminated: i) high risk mucosal HPV types, ii) low risk mucosal HPV types and iii) the remaining HPV types. Six clusters were formulated. Cluster A contains all known low risk HPV types. Cluster E and F contain almost all high risk HPV types, clusters B and C contain the remaining HPV types and cluster D contains both high risk HPV types and some of the remaining HPV types. Examples of the primers for each cluster are shown in table 1. (SEQ ID NO: 1 etc.) with and without tag.

The amplification of HPV E1 products is suitably performed with PCR or another method known those skilled in the art. Primers can be labeled, designed with a tag or not being labeled at all. In the latter two situations a second step is required to add a label to the amplification product. These techniques are also well known to a skilled person.

It has now surprisingly been found that the microarray technology can be successfully applied for the detection of one or more HPV types within a sample, thus enabling to analyse clinical samples at a much larger scale of operation. The presence of one or more HPV types within a sample is usually recognized within one day. The oligonucleotide DNA array technique according to the present invention works with high concentrations of all products. Different spots are characterized by HPV specific probes. Once the principle is established, the concentrations are optimized step by step in order to allow higher efficiency of the HPV array analysis.

The compositions of the primers and of the reagents used, are determined and optimized by routine experimentation. The detection mode may vary but the invention is practised conveniently with absorption microscopy and other modes such as fluorescence and laser scanning microscopy. Preferably, a fluorescence mode is used for reasons of quantitation, higher sensitivity, larger dynamic range, instead of extinction mode. The latter has the advantage that the outcome can be made visible with regular light microscopy.

General Applications Using the HPV Array Detection Method of the Invention
  detection of HPV infection
  detection of single or multiple infections in the same analysis Specific Applications
  to detect recurrence after treatment of cervical cancer or dysplasia.
  to detect HPV infection in cervical screening
  to detect HPV in case of cervical cytology with atypical cells of undetermined significance (ASCUS cells)
  to detect high risk type HPV in cervical epithelial abnormalities to detect the presence or absence of HPV in the differential diagnosis of carcinoma of unknown origin.
  Certain embodiments of the present invention are further detailed and illustrated below.

Generation of HPV Targets

In a preferred embodiment the target HPV sequences are labeled in an asymmetrical PCR reaction after a regular HPV type specific PCR amplification. As tag several options exist which are well known to a person skilled in the art. 5'-digoxigenin-modified reverse oligonucleotide primers recognizing a tag are used in the asymmetrical PCR. The primer concentrations may vary. Suitable concentrations are 0.05 and 1 µM for forward and reverse primers, respectively. Variations in these conditions are well known to a person skilled in the art.

In another embodiment other ways of amplification may be used as well. Examples are rolling circle PCR, nucleic acid sequence based amplification, transcription based mediated amplification. These are well known to a person skilled in the art.

In an alternative embodiment as label other options exist such as biotin. The choice may depend on the way capture oligonucleotides are attached to the solid support (see below).

In an alternative embodiment amplification products may be labeled internally using digoxigenin-11-dUTP replacing dTTP (or a mixture of the latter two nucleotides) in the amplification mixture of the PCR or other labels well known to a person skilled in the art.

In yet another alternative embodiment amplification products can be labeled directly with a fluorescent group (e.g. Cy-dyes, Fluorescein, Rhodamine, Texas Red) using modified reverse primers (end-labeled) or modified nucleotides (internal labeling) in PCR.

In other embodiments for labeling quantum dots, analogues allowing silver or gold type of staining reaction, nuclear analogues allowing infrared or interference based detection may be used. These are well known to a person skilled in the art.

In another embodiment to prepare single stranded DNA amplification products may be labeled in one of the above-mentioned ways using equal primer concentrations in the PCR reaction. In that case the double stranded DNA amplification products have to be denatured (e.g. by heat), quickly cooled on ice and used in the hybridization mixture. Other ways to prepare single stranded DNA after amplification may be used as well, These are well known to a person skilled in the art.

In a preferred embodiment amplification products may before a second amplification be purified after a first amplification procedure. This approach may be used after an initial amplification without label to subsequently label the amplification product.

Preparation of Microarrays

In general capture olignucleotides can be attached on different ways to a solid support or may be synthesized directly on the solid support by light directed synthesis.

In a preferred embodiment streptavidin coated slides are used as solid support for microarray analysis as disclosed in WO 02/44713, which is incorporated herein by reference. Streptavidin-coated microscope glass slides are used as a solid support in this microarray procedure.

In another embodiment other ways to attach capture probes to the solid support may be used. Examples are: crosslinking the DNA to the aminated (silanized) slides by baking the array at 80° C. for 24 hrs. UV crosslinking may be used as an additional step (also for: Poly-L-lysine coated slides); other solid supports as Amino-silane coated slides, Acrylamide coated slides, Epoxy-activated slides, Aldehyde activated slides, NHS ester activated slides, Hydrogel epoxy activated slides, Isothiocyanate activated slides, Mercaptosilane activated slides, Nitrocellulose-coated glass slides, well known to a person skilled in the art.

The concentration of 5' biotin-modified oligonucleotides may vary but in a preferred embodiment the concentration may be (12 µM, in 3× SSC/1.5 M Betaine)[SSC; 1× (8.76 g/L NaCl, 4.41 g/L sodium citrate, pH 7.0].

Several robots exits for the positioning of already synthesized oligonucleotides to the solid support. These are known to a person skilled in the art. We use a SDDC-2 array spotting robot from Engineering Services Inc.(ESI, Toronto, ON, Canada) and Stealth micro spotting pins (SMP3, ArrayIt). These pins are assumed to deliver ~0.6 nl volume at each spotting site, resulting in spots of ~100 µm in diameter according to the manufacturer.

In a preferred embodiment the spots on the slides were printed in triplicate for reasons quality control, but this may vary from one 10 or more. Spacing between the spots may vary depending on the software, but can be as small as 10 micron and be as large as with a dot spacing of 400 µm to more than 1 mm.

In a preferred embodiment we use a relative humidity between 45-60% during spotting varied and the temperature kept at 22° C., but these conditions may vary.

Spots containing a suspension of 5' biotin-modified DNA oligonucleotides are being printed on streptavidin glass slides using a commercially available microarray robot (SDDC-2, ESI/Virtek). We use 12 µM solutions of the biotinylated oligonucleotides for spotting but have shown that 6-20 µM of oligonucleotides in spotting solutions gave similar results.

In a preferred embodiment in the spotting buffer betaine may be added. The betaine concentration may vary but a concentration of 1.5 M to the 3× SSC is suitable. DNA spotting solutions we get clearly visible spots (by eye and by light microscopy) making this a point in the procedure to validate the quality of the array. After testing the quality of the array by this visual check, the betaine can be washed away for long term storage of the slides, without negative influence on the bound oligonucleotide, subsequent hybridization, or background after visualization.

In another embodiment spotting buffers without betaine may be used. These are well known to a person skilled in the art.

In a preferred embodiment 5' biotin-modified oligonucleotides were used for printing on the array. A 16-atom spacer arm has been used to attach the biotin group to the oligonucleotides, whereas a 12-atom spacer arm was used in the attachment between the digoxigenin (DIG) and the penultimate 5' terminal nucleotide. The spacer length may vary from 1 to 16 c-atoms.

Based on previous experience with K-ras the probes for HPV were designed similar to K-ras i.e. the biotin label with a spacer was directly coupled to a 20 mer HPV specific fragment. Initial experiments were not successful. Subsequently, the HPV specific fragment was increased to a length of 40 nucleotides. This resulted in stronger signals, but also increase in cross reactivity. Therefore, An additional spacer was necessary between the oligonucleotide with the biotin spacer and the HPV specific fragment, in addition, the 40-mer HPV may be reduced in size with resulting improvement of quality since cross reactivity may be diminished. Primers and probes are presented in Table 1 below.

TABLE 1

Oligonucleotide sequences related to amplification (cluster a-F) and capturing HPV 1-85

| SEQ ID NO | SEQUENCE | USE | Cluster |
|---|---|---|---|
| 1 | GTGCCAGGAW CAGTTGTTAG | Amplification primer | A |
| 2 | CAWKTGHATT TCAATDGC | Amplification primer | A |
| 3 | CAGTTGTTAG AACTKTATGA | Amplification primer | A |
| 4 | TCYTGYAAHG TCCAHGGYTC | Amplification primer | A |
| 5 | GAAATSVTTY TTYMRAAGGT | Amplification primer | B |
| 6 | TCCTGGCACR CATCTAAACG | Amplification primer | B |
| 7 | TTTBHAAATV CATTTCCAWT WGA | Amplification primer | D |
| 8 | TAAACGHTKR SAHAGNKTCT CCAT | Amplification primer | D |
| 9 | CCTTTTTCTC AAGGACGTGG | Amplification primer | E |
| 10 | CDTGGTSCAR ATTAGAYTTG | Amplification primer | F |
| 11 | GNHGGHACCA CBTGGTGG | Amplification primer | E + F |
| 12 | CITGGTICAI ATTAGAITTG | Amplification primer | F |
| 13 | GIIGGIACCA CITGGTGG | Amplification primer | E + F |
| 14 | TWGSIYTIIT IGATGAYGYI AC | Amplification primer | C |
| 15 | TIGSIYTIWT RGATGATGCI AC | Amplification primer | C |
| 16 | TIGSIYTIIT IGATGAYGYI AC | Amplification primer | C |
| 17 | GATTTCCAGC TTTGGTCAGT | Amplification primer | C |

TABLE 1-continued

Oligonucleotide sequences related to amplification
(cluster a-F) and capturing HPV 1-85

| SEQ ID NO | SEQUENCE | USE | Cluster |
|---|---|---|---|
| 18 | CCAMARCCTT TYAAARAAAG AIKYCCA | Amplification primer | C |
| 19 | SMAARYTTKI KRAAAAAASA IKTCCA | Amplification primer | C |
| 20 | TNGSNYTNHT DGATGAYGYN AC | Amplification primer | C |
| 21 | SSMMARYYTK HBRAARAAAS ABKYCCA | Amplification primer | C |
| 22 | CCAMARCCTT TYAAARAAAG ABKYCCA | Amplification primer | C |
| 23 | VMAARYTTKH KRAAAAAASA BKTCCA | Amplification primer | C |
| 24 | TTTTCTTTTC TTTTCAGAGG AGCAGGACGA CAATG | Probe HPV2 | |
| 25 | TTTTCTTTTC TTTTCTGAAG ACGAGGAGGA CAATG | Probe HPV3 | |
| 26 | TTTTCTTTTC TTTTCCCATT AAAGGTGTCC GAAGC | Probe HPV6 | |
| 27 | TTTTCTTTTC TTTTCAGATG TGTCAAAAGC CAAAG | Probe HPV7 | |
| 28 | TTTTCTTTTC TTTTCCGAGG AGGAGCATGG AAACC | Probe HPV10 | |
| 29 | TTTTCTTTTC TTTTCCCATT AACTGTGTCA GAGAC | Probe HPV11 | |
| 30 | TTTTCTTTTC TTTTCATTGA CAGTATCACA AGCTA | Probe HPV13 | |
| 31 | TTTTCTTTTC TTTTCCAGAC CTACGTGACC ATATA | Probe HPV16 | |
| 32 | TTTTCTTTTC TTTTCACATG GCATACAGAC ATTAA | Probe HPV18 | |
| 33 | TTTTCTTTTC TTTTCGAGGA AAATGGAAAC CCTAG | Probe HPV28 | |
| 34 | TTTTCTTTTC TTTTCTAGTA AACGACTTTG TGATC | Probe HPV31 | |
| 35 | TTTTCTTTTC TTTTCAGCAC TGGAAATATC CAGGG | Probe HPV32 | |
| 36 | TTTTCTTTTC TTTTCCTTTA TTGTATACAG CCAAA | Probe HPV33 | |
| 37 | TTTTCTTTTC TTTTCAGTAA TGGAAATCCA CTATA | Probe HPV34 | |
| 38 | TTTTCTTTTC TTTTCTAGCA CATGTTTGTC TGATC | Probe HPV35 | |
| 39 | TTTTCTTTTC TTTTCAGAAT ACTATGAACA AGACA | Probe HPV39 | |
| 40 | TTTTCTTTTC TTTTCAGATG TTTCAAAGGC TAAAG | Probe HPV40 | |
| 41 | TTTTCTTTTC TTTTCAACAT TGGAAACATG TAGAG | Probe HPV42 | |
| 42 | TTTTCTTTTC TTTTCGAAAT GTATACGATA TGAAT | Probe HPV44 | |
| 43 | TTTTCTTTTC TTTTCACATG GTATTACCAA ACTAA | Probe HPV45 | |
| 44 | TTTTCTTTTC TTTTCTTTTG TTTTACAAAG CAAAG | Probe HPV52 | |
| 45 | TTTTCTTTTC TTTTCTTTAG CGCTGAACGA CAACG | Probe HPV54 | |
| 46 | TTTTCTTTTC TTTTCTGTTA TTACACAAAG CAAAG | Probe HPV55 | |
| 47 | TTTTCTTTTC TTTTCGTTTC TTTACAAGGA CGTGG | Probe HPV56 | |
| 48 | TTTTCTTTTC TTTTCAGAGG ATCAGGAAGA CAATG | Probe HPV57 | |
| 49 | TTTTCTTTTC TTTTCCTATA ATGTATACAG CCAGA | Probe HPV58 | |
| 50 | TTTTCTTTTC TTTTCAGACA TTAATGAACA CATAA | Probe HPV59 | |
| 51 | TTTTCTTTTC TTTTCAGAGG GATCTGATCA ACAGG | Probe HPV61 | |
| 52 | TTTTCTTTTC TTTTCCTTTG TATTATAAAG CTAAA | Probe HPV67 | |
| 53 | TTTTCTTTTC TTTTCAGTTT TTTTTCCACC ACTTG | Probe HPV69 | |
| 54 | TTTTCTTTTC TTTTCAGAAC ATTATGAACA GGACA | Probe HPV70 | |

TABLE 1-continued

Oligonucleotide sequences related to amplification
(cluster a-F) and capturing HPV 1-85

| SEQ ID NO | SEQUENCE | USE | Cluster |
|---|---|---|---|
| 55 | TTTTCTTTTC TTTTCAGAGG GACCTGACGA ACAGG | Probe | HPV72 |
| 56 | TTTTCTTTTC TTTTCAGTAA TGGGAACCCA CTATA | Probe | HPV73 |
| 57 | TTTTCTTTTC TTTTCTATAT GCACTAAATG ATGTA | Probe | HPV82 |
| 58 | TTTTCTTTTC TTTTCTTTAG AATTGCATCA AGAGG | Probe | HPV83 |
| 59 | TTTTCTTTTC TTTTCAACAT TACGAGACTG ATAGT | Probe | HPV85 |

In a preferred embodiment the 5'-Biotin-modified capture oligonucleotides have a length of 35 nucleotides. The 5'end of the oligonucleotide sequence starts with a 15-mer that contains a triple [TTTTC] repeat, followed by a stretch of HPV type-specific nucleotides. The length of the first part with repeats may vary from no repeat (i.e. 0 nucleotides) to more than 10 repeats. This part has a second spacer function and optimizes hybridization. In our hands the repeats is sufficient for a suitable signal. In addition, nucleotide composition may be other than TTTTC, but need to be selected in such a way that no cross hybridization occurs with other relevant DNA fragments in the assay. For one HPV specific capture probe the spacer length does not need to be constant, but may vary as well.

In a preferred embodiment the HPV specific sequences have a length of 20 nucleotides. These were chosen from multisequence alignments after ordering and clustering all HPV E1 gene sequences and blasted against all collaborate NCBI nucleotide databases to check for their uniqueness among HPV strains (NCBI: national center for biotechnology information). Within the HPV-specific sequence of the capture oligonucleotides of two closely related types at least 1 but preferably 2 positions are unique to a HPV type.

In another embodiment the length of the HPV specific 20 nucleotides may vary. This may be shorter, longer or combinations of different lengths may be used.

In another embodiment the capture probes consist of 5' modified peptide nucleic acids (PNA). These can be used for their high affinity binding. Also a combination of 5' modified oligonucleotides and PNA may be present on the array.

For purposes of recognition the where the spots are located on the slide we used marker oligonucleotides with a 5' biotin-modified oligonucleotides of 40 nucleotides in length with a digoxigenin-modification at the penultimate 3' terminal nucleotide. But the length of this marker oligonucleotide may vary and be longer or shorter.

In another embodiment the oligonucleotide sequence may be complementary to the ones defined in the table. This holds for the primer and probes.

Spotted arrays were kept in a dry and cold place (refrigerated) until use. Arrays have been stored for over 3 months and gave results similar to new arrays.

Hybridization

In a preferred embodiment the printed arrays are washed before hybridization in phosphate-buffered saline [PBS; 1× (0.21 g/L KH2PO4, 9 g/L NaCl, 0.73 g/L Na2HP)4*7H2O, pH 7.4)] containing 0.5 mL/L Tween 20 for 10 min to remove unbound materials. Other washing buffers are suitable as well known to a person skilled in the art.

In a preferred embodiment disposable coverplates (Shandon) were used for all hybridizations, incubations, wash and immunochemical detection steps. Glass microscope slides fit in these coverplates and are held in a vertical position during the whole procedure. There is a 80 micron space on top of the slide when fixed in the coverplate (approximate volume of 80 µl) and the incubation mixture is being retained by capillary forces. Washing the slides is simply performed by adding PBS-T to the upper buffer reservoir (approximately 3 ml) and have it pass the array.

In another embodiment other slide holders can be used or the slide can be incubated in horizontal fashion. In these situations the amount of hybridization fluid may vary.

In a preferred embodiment the microarrays were prehybridized in a buffer containing 3.3× SSC/1.7 mM EDTA/17 mM Hepes/0.12% Tween 20 pH 7.3 for 5 min at RT and hybridized in the same solution with probe for 1 h at 22° C. The probe hybridization solution contained 40% v/v of the unpurified total PCR products of the asymmetrical PCR per hybridization in the same buffer, but this 40% ratio may vary. Hybridization incubation was performed for 1 h at RT (around 22° C.), but the time and temperature may vary. The hybridization mixture may a composition of different PCR reactions and the hybridization buffer. Or for different PCR reactions serial hybridization may be performed.

In another embodiment other hybridization buffers and temperatures may be used. These are well known to a person skilled in the art.

In a preferred embodiment washing after hybridization is performed to decrease cross-hybridization of target to mismatched capture oligonucleotides. Five subsequent washes of 5 min. each are performed at room temperature PBS-Tween 20 (0.05%); 2× SSC/0.1% SDS; 1× SSC/0.1% SDS; 0.1× SSC; 0.05× SSC.

In another embodiment the wash procedure after hybridization may be performed at other, usually higher, temperatures.

In a preferred embodiment the HPV array is designed with a visual control probe (VCP) containing biotine label on the 5' end and a visualization hapten on the penultimate 3' end. In fact this is an internal positive control for the visualization procedure and may also provide information about the position of the HPV specific probes and other negative control probes. The VCP may be spotted at various concentrations providing information about the dynamic range of the visualization procedure for each experiment.

In another embodiment other control probes may be sued as well. These are well known to a person skilled in the art.

Visualization Procedure

In a preferred embodiment as a control for hybridization to the hybridization mixture an antisense Cy3-labeled oligonucleotide may be added, that recognizes the 15-nucleotide stretch preceding the HPV-specific sequence of the capture oligonucleotides. The length of this array may be longer dependent on the length of the second spacer or shorter.

In another embodiment this antisense oligonucleotide may be added to the array after the Dig-detection and visualization, followed by a short PBS-T wash step.

In a preferred embodiment the after hybridization and washing on the array remaining digoxigenin groups of the labeled PCR products were incubated by a 1:100 dilution of a mouse monoclonal antibody to digoxigenin (Anti-digoxigenin clone 1.71.256, Roche Molecular Biochemicals, Almere, The Netherlands) according to the manufacturers protocol, followed by a 45 min. incubation with a 1:20 dilution of alkaline phosphatase-conjugated rabbit anti-mouse immunoglobulins (DAKO, Amsterdam, The Netherlands). The Vector Blue alkaline phosphatase substrate kit (SK-5300, Vector Laboratories, Burlingame, Calif., USA) was used to detect alkaline phosphatase activity according to the manufacturer's instructions. Vector Blue produces a blue reaction product that can be seen using brightfield or fluorescent microscopy. Slides analysed with light microscopy (absorption mode) were mounted with an aqueous-based mounting medium Imsol Mount (Klinipath, Duiven, The Netherlands). Slides analysed with laser scanner (fluorescence mode) were washed twice for 5 min. in PBS containing 0.5 mL/L Tween 20, rinsed in water, washed for 3 min in ethanol 100% and air-dried in the dark. The Vector Blue reaction product is detected as a red fluorescence using a laser that excites at 635 m wavelength. The chemical substances mentioned above are not restrictive in any sense but examples of components that may be used for adequate result.

In another embodiment other visualization chemistries can be used which are well known to a person skilled in the art. An example is the Vector Red alkaline phosphatase substrate kit (SK-5100), that may be used to give red spots in brightfield microscopy and green spots in fluorescence detection mode (at 532 nm excitation).

Imaging and Data Analysis

In a preferred embodiment slides with fluorescent mode were scanned with Microarray laserscanner Genepix 4000A and data analysis was performed with GenePix Pro 3.0 software from Axon Instruments Inc. (Foster City, Calif.). Scans show an image of the whole array without losing the overall image. This scanner uses a 532 nm laser to excite Cy3 and a 635 nm laser to excite Cy5. The green laser light of the 532 nm laser was also used to excite the reaction product of alkaline phosphatase and Vector Red and the light of the 635 nm laser was used to excite the reaction product of Vector Blue and alkaline phosphatase. Sixteen-bit TIFF images of 10 μm resolution were subtracted for local background intensity. The software does not normalize the data. The median of the feature intensities of three spots were used to calculate mean signal intensities for each DNA concentration spotted. Slides with absorption mode were also semiquantitatively analysed by regular light microscopy (using 25× total magnification).

In another embodiment slides may be photographed with a CCD camera attached onto a light microscope. When using specific adaptors or low-magnification lenses, the whole array can be viewed and documented in one shot. Other commercially available systems may be used as well and may easily be determined by a person skilled in the art.

In a preferred embodiment the array is visualized with conventional bright field microscopy. Thus the abovementioned scanners are not obligatory for analysis. This set up allows the use of the HPV array in any modem pathology laboratory that PCR and immunohistochemistry facilities.

In another embodiment infrared, phase contrast or interference based methods may be sued for imaging. These are well known to a person skilled in the art.

Although the present invention is herein described in certain typical embodiments, it will be understood that variations may be made without departing from the spirit of the invention. For example, the HPV DNA array according to the invention is typically described herein using alkaline phosphatase for detection with absorption microscopy. Evidently, for visualization purposes this enzyme may be replaced by a fluorescent substance or other known detectable group. This needs to be put in perspective of the usually microscopic detection system used. The test characteristics of the system may be dependent of the combination used. Such variations are evident to the man skilled in the art, are all encompassed within the scope of the present invention.

The present disclosure is to be considered as in all respects illustrative and not restrictive, the scope of the invention being indicated by the appended Claims, and all changes which come within the meaning and range of equivalency are intended to be embraced therein.

The invention claimed is:

1. A method of detecting the presence of HPV in a sample comprising the following steps:
- amplifying and labeling part of the E1 HPV gene, wherein amplification is performed using a primer pair selected from the group consisting of SEQ ID NO:1/SEQ ID NO:4, SEQ ID NO:2/SEQ ID NO:4, SEQ ID NO:3/SEQ ID NO:4, SEQ ID NO:5/SEQ ID NO:6, SEQ ID NO:7/SEQ ID NO:8, SEQ ID NO:9/SEQ ID NO: 11, SEQ ID NO:9/SEQ ID NO:13, SEQ ID NO:10/SEQ ID NO:11, and SEQ ID NO:12/SEQ ID NO:11 to thereby form a labeled fragment;
- hybridizing the labeled fragment to a solid support upon which a plurality of HPV E1-gene specific capture probes are immobilized, wherein the HPV E1-gene specific capture probes are selected from the group consisting of SEQ ID NO:24 to SEQ ID NO:59, and wherein the HPV E1-gene specific capture probes are optionally immobilized on the support as synthesized oligonucleotides or are optionally built on the support by light-directed oligonucleotide synthesis;
- removing uncaptured labeled fragments; and
- detecting the captured labeled fragment, wherein detection of the fragment indicates presence of HPV in the sample.

2. The method according to claim 1 wherein the step of amplification and labeling further comprises amplifying and labeling an HPV gene in addition to the HPV E1 gene.

3. A kit comprising:
- a device suitable for carrying out the detection method according to the present invention as claimed in any one of claim 1 or claim 2;
- a primer pair selected from the group consisting of SEQ ID NO:1/SEQ ID NO:4, SEQ ID NO:2/SEQ ID NO:4, SEQ ID NO:3/SEQ ID NO:4, SEQ ID NO:5/SEQ ID NO:6, SEQ ID NO:7/SEQ ID NO:8, SEQ ID NO:9/SEQ ID NO:11, SEQ ID NO:9/SEQ ID NO:13, SEQ ID NO:10/SEQ ID NO:11, and SEQ ID NO:12/SEQ ID NO:11;
- one or more solid supports containing HPV E1-gene specific capture probes selected from the group consisting of SEQ ID NO:24 to SEQ ID NO:59; and
- an optional reagent for signal enhancement.

4. The method of claim 1 wherein amplification is performed using at least two primer pairs thereby producing a second labeled fragment, and wherein the labeled fragment and the second labeled fragment belong to different HPV risk types.

5. The method of claim 1 wherein the plurality of HPV E1-gene specific capture probes includes at least three of SEQ ID NO:26, SEQ ID NO:29, SEQ ID NO:40, SEQ ID NO:41, SEQ ID NO:42, SEQ ID NO:45, SEQ ID NO:51, SEQ ID NO:54, and SEQ ID NO:55.

6. The method of claim 1 wherein the plurality of HPV E1-gene specific capture probes includes at least three of SEQ ID NO:31, SEQ ID NO:32, SEQ ID NO:34, SEQ ID NO:36, SEQ ID NO:38, SEQ ID NO:43, SEQ ID NO:44, and SEQ ID NO:49.

7. A method of detecting the presence of HPV in a sample comprising the following steps:
- amplifying and labeling part of the E1 HPV gene to thereby form a labeled fragment, wherein the amplification is performed such that the labeled fragment has a sequence capable of hybridizing with at least one of a plurality of HPV E1-gene specific capture probes;
- wherein the HPV E1-gene specific capture probes are selected from the group consisting of SEQ ID NO:24 to SEQ ID NO:59;
- hybridizing the labeled fragment to a solid support upon which the HPV E1-gene specific capture probe is immobilized;
- removing uncaptured labeled fragments; and
- detecting the captured labeled fragment, wherein detection of the fragment indicates presence of HPV in the sample.

8. The method of claim 7 wherein amplification is performed using at least two primer pairs selected from the group consisting of SEQ ID NO:1/SEQ ID NO:4, SEQ ID NO:2/SEQ ID NO:4, SEQ ID NO:3/SEQ ID NO:4, SEQ ID NO:5/SEQ ID NO:6, SEQ ID NO:7/SEQ ID NO:8, SEQ ID NO:9/SEQ ID NO:1 1, SEQ ID NO:9/SEQ ID NO:13, SEQ ID NO:10/SEQ ID NO:11, and SEQ ID NO:12/SEQ ID NO:11, thereby producing a second labeled fragment, and wherein the labeled fragment and the second labeled fragment belong to different HPV risk types.

9. The method of claim 7 wherein the solid support comprises at least three of SEQ ID NO:26, SEQ ID NO:29, SEQ ID NO:40, SEQ ID NO:41, SEQ ID NO:42, SEQ ID NO:45, SEQ ID NO:51, SEQ ID NO:54, and SEQ ID NO:55.

10. The method of claim 7 wherein the solid support comprises at least three of SEQ ID NO:31, SEQ ID NO:32, SEQ ID NO:34, SEQ ID NO:36, SEQ ID NO:38, SEQ ID NO:43, SEQ ID NO:44, and SEQ ID NO:49.

* * * * *